United States Patent
Schadt et al.

(10) Patent No.: US 9,206,140 B2
(45) Date of Patent: Dec. 8, 2015

(54) WATER RECYCLING IN A MELAMINE PRODUCTION PROCESS

(75) Inventors: Arne Schadt, Pasching (AT); Robert Schlesinger, Linz (AT); Gregor Demel, Linz (AT); Christoph Neumüller, Ennsdorf (AT); Franz Hintermüller, Bad Leonfelden (AT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 13/500,950

(22) PCT Filed: Oct. 8, 2010

(86) PCT No.: PCT/EP2010/065080
§ 371 (c)(1),
(2), (4) Date: Jul. 2, 2012

(87) PCT Pub. No.: WO2011/042532
PCT Pub. Date: Apr. 14, 2011

(65) Prior Publication Data
US 2012/0271050 A1    Oct. 25, 2012

(30) Foreign Application Priority Data
Oct. 9, 2009    (EP) ..................................... 09172664

(51) Int. Cl.
*C07D 251/60* (2006.01)
*C07D 251/62* (2006.01)

(52) U.S. Cl.
CPC ............ *C07D 251/60* (2013.01); *C07D 251/62* (2013.01)

(58) Field of Classification Search
CPC ............................ C07D 251/62; C07D 251/60
USPC .................................................. 544/203, 201
See application file for complete search history.

(56) References Cited

U.S. PATENT DOCUMENTS

| | | | |
|---|---|---|---|
| 7,176,309 B2 * | 2/2007 | Schroder et al. | ............... 544/203 |
| 7,741,481 B2 | 6/2010 | Ruech | |
| 2005/0131228 A1 * | 6/2005 | Schroder et al. | ............... 544/203 |
| 2009/0062535 A1 | 3/2009 | Toplack et al. | |
| 2009/0294272 A1 | 12/2009 | Ruech et al. | |

FOREIGN PATENT DOCUMENTS

| | | |
|---|---|---|
| EP | 1775264 A1 | 4/2007 |
| EP | 2098516 A1 | 9/2009 |
| IT | 1282369 A1 | 7/1997 |
| IT | 1282370 B1 | 3/1998 |
| WO | 0018684 A1 | 4/2000 |
| WO | 0064812 A1 | 11/2000 |
| WO | 0146159 A2 | 6/2001 |
| WO | 02100839 A1 | 12/2002 |
| WO | 2005100327 A1 | 10/2005 |
| WO | 2006042760 A1 | 4/2006 |
| WO | 2006081626 A1 | 8/2006 |
| WO | 2006117243 A1 | 11/2006 |
| WO | 2006133966 A1 | 12/2006 |
| WO | 2007119156 A2 | 10/2007 |
| WO | 2009007813 A1 | 1/2009 |

* cited by examiner

*Primary Examiner* — Venkataraman Balasubramanian
(74) *Attorney, Agent, or Firm* — The Webb Law Firm

(57) ABSTRACT

The present invention relates to a method for recycling water in a melamine production process comprising—a wet process comprising the steps of aqueous treatment of a melamine melt from a melamine synthesis plant with an aqueous alkali containing solution and crystallization for producing solid melamine and a triazine containing alkaline mother liquor,—a wastewater treatment process comprising the steps of thermal treatment of said triazine containing alkaline motor liquor, and—a recycling process, whereby at least parts of the thermally treated alkaline mother liquor are being recycled to the wet process.

16 Claims, 9 Drawing Sheets

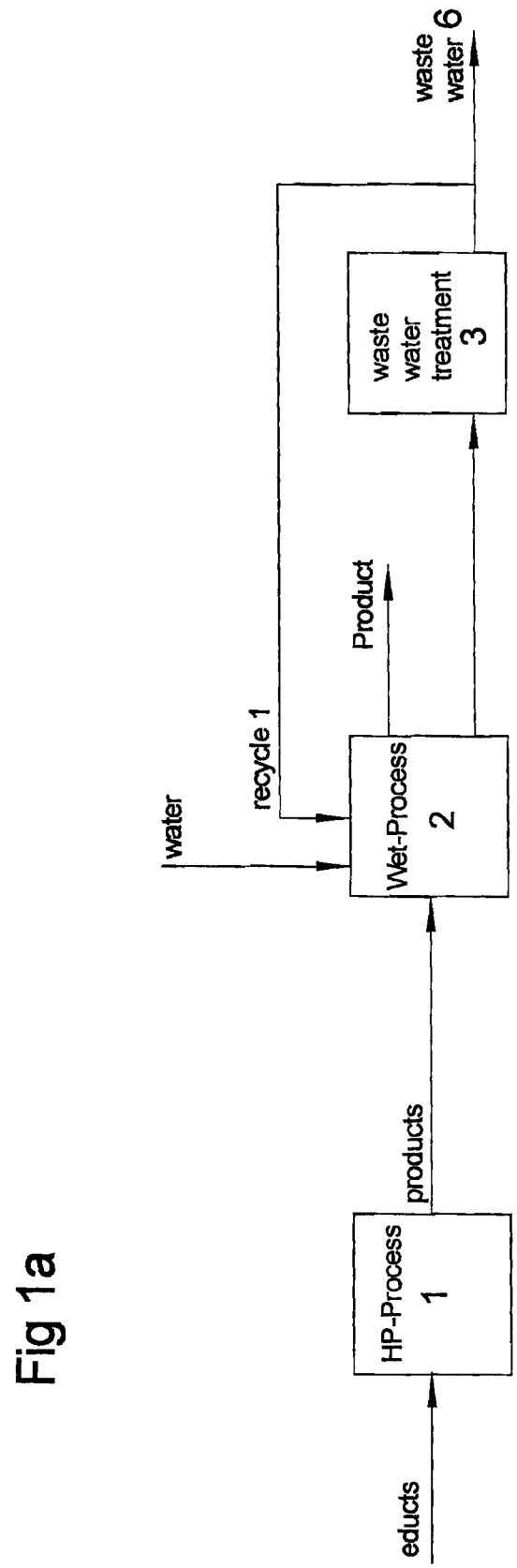

WATER RECYCLING IN A MELAMINE PRODUCTION PROCESS

BACKGROUND OF THE INVENTION

1) Field of the Invention

The invention relates to method for recycling water in a melamine production process.

2) Description of the Prior Art

The starting material used for melamine preparation is virtually exclusively urea, which is converted to melamine either in a catalytic low-pressure process or in a high-pressure process without catalyst.

The high pressure process is mainly conducted in a melamine plant comprising a high-pressure part, a wet process for melamine purification and waste water treatment.

Melamine purification is usually necessary since by-products, degradation products and unconverted starting materials are present in the crude melamine. Since the melamine workup is typically affected in the presence of water, these by-products are obtained as wastewater constituents, for example as constituents of the mother liquor from the melamine crystallization.

The wet process usually comprises the steps of quenching the melamine melt with an aqueous phase and subsequent melamine crystallization. In order to obtain melamine of high quality an alkali containing quenching solution is used. The alkaline mother liquor can be subsequently either recycled or undergoes a treatment for removing melamine, by-products and degradation products.

Typically, the wastewater of a melamine plant comprises triazines, for instance the oxoaminotriazines ammeline and ammelide, melamine, melam, cyanomelamine, ureidomelamine, cyanuric acid, and also ammonia, carbon dioxide, urea and possibly NaOH in different amounts.

The prior art discloses some processes for treating triazine-containing melamine wastewaters and the recycling of the purified water to the melamine plant.

According to WO 01/46159 A2, the mother liquor comprising melamine and OATs is acidified up to pH=7 after the melamine crystallization, which forms an OAT suspension which is then subjected to a tangential filtration. This affords an aqueous melamine solution and a OAT dispersion. While the aqueous melamine solution is recycled into the process, the OATs are separated from the dispersion.

A further means of wastewater treatment in melamine plants consists in treating the wastewaters in a thermal wastewater treatment plant (TAA), where the triazine-containing wastewater ingredients are hydrolysed under high pressure and high temperature in the liquid phase to $CO_2$ and $NH_3$. Such a process is described, for example, in IT 01282370. There, the crystallization mother liquors of a melamine plant are heated to 180 to 250° C. in a closed vessel under the autogenous pressure of the system, subsequently cooled down, $CO_2$ is added till a pH-value of 6-8 is reached and the thus formed precipitation is separated off from the treated mother liquid.

In a similar manner, according to IT 01282369, triazine-containing melamine wastewater is treated in a closed vessel at a temperature of >250° C. The $NH_3$ and $CO_2$ formed is subsequently stripped off and the resulting pure liquid is recycled into the plant or discharged.

WO 02/100839 A1 describes a process in which the quenching process is conducted by using $NH_3$ containing water. The majority of the mother liquors of the melamine crystallization are recycled untreated into the melamine plant; $NH_3$ and OAT are recovered from the smaller portion of the mother liquors. The disadvantage of this process is that more fresh water additionally has to be supplied when the untreated, OAT-containing mother liquors are recycled into the melamine process in order to be able to work up the crude melamine melt to the desired quality.

WO 2006/042760 A1 provides a process for treating triazine-containing water of a melamine plant whereby the water is fed to at least one membrane filtration unit (MF), the water is separated in the membrane filtration unit (MF) into a fraction rich in ionic triazines and a fraction rich in nonionic triazines, and then the fraction rich in ionic triazines is discharged and the fraction rich in nonionic triazines is recycled into the melamine plant.

WO 2006/133966 provides a thermal process for cleaning wastewaters of a melamine plant, in which triazine-containing wastewater is subjected to a thermal pretreatment stage to form a gas phase and a liquid phase, the liquid phase of the thermal pretreatment stage is subjected to a thermal hydrolysis stage and finally $NH_3$ is removed from the resulting $H_2O$-, $CO_2$- and $NH_3$-containing liquid phase in a stripping stage. The thus obtained $NH_3$-free liquid phase is either discharged or recycled. In the specific case that the aqueous workup part of the melamine plant proceeds in the presence of NaOH, the $H_2O$-rich bottom phase contains sodium carbonate and can therefore not be recycled into the melamine process.

The quality of the recycled waste water e.g. pH or salt content depends strongly on the applied treatment methods. Thus, it is still often necessary to add fresh water and/or fresh alkaline solution to the wet process in order to maintain the desired quality of the produced melamine.

SUMMARY OF THE INVENTION

It is accordingly an object of the invention to provide a method which allows for a further reduction of fresh water and/or alkaline solution, in particular NaOH solution, which is usually added to the wet process.

The present invention accordingly provides a method for recycling water in a melamine production process comprising
 a wet process comprising an aqueous treatment of a melamine melt from a melamine synthesis plant with an aqueous alkali containing solution and a subsequent crystallisation for providing solid melamine and a triazine containing alkaline mother liquor,
 a thermal treatment process comprising the thermal treatment of said triazine containing alkaline mother liquor, and
 a recycling process, whereby at least parts of the thermally treated alkaline mother liquor are being recycled to the wet process.

In an exemplary embodiment of the present method the aqueous treatment comprises quenching of a melamine melt from a melamine synthesis plant, preferably after off-gas separation, with an aqueous alkali containing solution, in particular NaOH or KOH solution.

Before quenching oxoaminotriazines and condensation products can be completely or in part removed from the melamine melt. Quenching of melamine melt can be carried out at temperatures between 100 to 160° C., preferably 130 to 150° C. and at a pressure between 1 and 7 bar, preferably 4 and 6 bar. Preferably an alkaline quenching solution containing 0.05 to 0.5 wt % alkali is used.

In the quenching step an aqueous solution of melamine and byproducts is received, which subsequently is subjected to the crystallization step where solid melamine and a triazine containing alkaline mother liquor are obtained.

In the following thermal treatment process said triazine containing alkaline mother liquor is hydrolized under high temperature and high pressure in order to decompose the triazines to $CO_2$ and $NH_3$. Preferably, the thermal hydrolysis takes place at a temperature of 200 to 260° C. and a pressure of 30 to 100 bar. The heat necessary for the hydrolysis for example is supplied by steam as a heat carrier into the hydrolysis apparatus, the heat typically being transferred in indirect form.

In the thermal hydrolysis stage, an $H_2O$-, $CO_2$- and $NH_3$-containing liquid phase is obtained. The reaction takes place in the liquid phase, whereas minor losses due to evaporation cannot be avoided. $NH_3$ is advantageously removed from this liquid by stripping with steam, so that $NH_3$-free $H_2O$ which contains $CO_2$ in the form of sodium carbonate and sodium hydrogen carbonate can be removed at the bottom of the stripper. The $NH_3$-rich vapours are returned into the melamine plant or into the urea plant. The thermally treated and stripped mother liquor has preferably a pH between 9 and 12.

In one exemplary embodiment prior to the thermal hydrolysis stage a thermal pretreatment stage is installed. In the thermal pretreatment stage the triazine containing alkaline mother liquor from the melamine crystallization is heated to form a gas phase and a liquid phase. Then the vapours from the gas phase of the thermal pretreatment stage are condensed and the liquid phase of the thermal pretreatment stage is subjected to a thermal hydrolysis stage and $NH_3$ is removed via stripping from the resulting $H_2O$-, $CO_2$- and $NH_3$-containing liquid phase. The temperature in the thermal pretreatment stage is preferably 140 to 250° C., more preferably 180 to 220° C. The pressure in the thermal pretreatment stage can be between 5 and 50 bar, more preferably between 15 and 30 bar.

Up to 80 wt %, preferably 10 to 80 wt %, of the thermally treated alkaline mother liquor, in particular stripped alkaline mother liquor, removed from the bottom of the stripper are preferably recycled to the wet process, in particular to the quenching stage or crystallisation stage. The part of the thermally treated alkaline mother liquor, in particular stripped alkaline mother liquor, which is not being recycled to the wet process is with or without further treatment preferably discharged as wastewater.

The thermally treated alkaline mother liquor, in particular stripped alkaline mother liquor mostly contains sodium carbonate and sodium hydrogen carbonate. The recycling of it to the melamine process allows for the reduction of the amount of added alkali, in particular NaOH, required in the wet process. The recycling of thermally treated alkaline mother liquor, in particular stripped alkaline mother liquor, does not disturb the chemical balance of the mother liquor (ML) used for quenching in respect to its pH and concentration of free hydroxid anions.

In the specific case that the aqueous workup part of the melamine plant proceeds in the presence of NaOH, the $H_2O$-rich bottom phase containing sodium carbonate which was previously discharged can now be recycled into the melamine process.

Further advantages are related to the recycling of the thermally treated melamine waste water of the present method. They include cost savings by reducing the amount of discharged wastewater which is especially important for melamine plants set up in dry regions where water preparation and water availability is limited or expensive. Besides that savings in the fresh water and fresh NaOH demand are likewise a consequence of the process of the invention.

In another preferred embodiment the thermally treated alkaline mother liquor, in particular stripped alkaline mother liquor, is subjected to filtration before at least parts of it are being recycled to the wet process. In this case the alkaline liquor is fed to at least one membrane filtration unit (MF), is separated in the membrane filtration unit (MF) into a permeate consisting essentially of pure water and a retentate containing the sodium carbonates in dissolved form. At least parts of the permeate are subsequently recycled to the wet process, whereas the retentate can be discharged as waste water.

The membrane filtration unit may comprise one or more filtration stages. In a multistage membrane filtration unit, the permeate of the first membrane filtration unit is fed to at least one further membrane filtration unit. In a multistage filtration, higher purities of the permeate are achieved. It is also possible in a multistage membrane filtration unit to use membrane modules with different separation properties. In this way, it is possible to achieve optimal degrees of separation according to the composition of the triazine-containing water. The retentates of the individual membrane filtration units can be combined or each fed alone to its further use.

It is preferred if the membrane filtration unit comprises an ultrafiltration stage and/or a reverse osmosis stage. In the process of ultrafiltration particles that would cause fouling from the waste water feed are removed prior to reverse osmosis.

Reverse osmosis is preferably carried out at a pressure of up to about 100 bar, which is above the osmotic pressure of the solution. The reverse osmosis splits the wastewater into the permeate that is nearly free from dissolved species, in particular $Na_2CO_3$ and $NaHCO_3$, and the retentate that contains most of the dissolved species with significantly higher concentrations than in the waste water feed.

The implementation of a membrane filtration unit allows for a recycling to a larger amount than without such a filtration step, as the recycled filtration permeate is nearly free from sodium carbonate and sodium hydrogen carbonate but consists essentially of pure water. This means that a recycling rate of up to 80%, preferably 50 to 80%, relating to the total amount of thermally treated alkaline mother liquor and considerable savings in fresh water demand are achieved.

The recovery and work-up of alkaline mother liquor or wastewater is also possible with a reactive treatment, where alkaline compound added the in the wet process, e.g. NaOH can be recovered selectively and high amounts of water can be recycled. The reactive regeneration of NaOH works as follows:

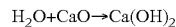

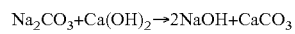

Therefore, in another preferred embodiment the thermally treated alkaline mother liquor, in particular stripped alkaline mother liquor, containing sodium carbonate is subjected to causticisation before at least parts of it are being recycled to the wet process. Caustification processes are known for instance from EP 1 775 264 A1 or WO 00/64812 A1.

In a first step preferably 10 to 50 g/l, in particular 20 to 30 g/l, $Ca(OH)_2$ or lime CaO, in particular slaked lime are added to the alkaline liquid phase. The causticised solution is allowed to react for a certain time at a temperature between 20° C. and 130° C., preferably 70 to 100° C. whereupon lower temperatures are preferred in terms of the solubility of CaO whereas higher temperatures are preferred in terms of the kinetics of the reaction. The causticised solution is subjected to a solid separation step, in particular filtration step where Ca(OH)$_2$ and CaCO$_3$ are separated. The residual solids are preferably collected and used in other processes.

The NaOH enriched supernatant is then at least partially recycled to the wet process. This allows for a reduction of NaOH consumption as alkali containing solution for the quenching process of up to 70 wt % NaOH, preferably 10 to 70 wt % NaOH. The supernatant which is not recycled is discharged as waste water.

In yet another preferred embodiment the recycling of water in a melamine process combines all the above described methods.

In this case the part of the waste water which is not recycled to the wet process after leaving the bottom of the stripper and otherwise discharged is fed to and separated in a membrane filtration unit (MF) into a permeate and a retentate, whereby the permeate which contains pure water is recycled to the wet process. The retentate leaving the membrane filtration unit and containing the dissolved carbonates in high concentrations is then causiticised. The causticised solution is subjected to a solid separation step, in particular precipitation or filtration, and the NaOH enriched supernatant is recycled to the wet process.

A combination of the aforesaid recycling methods allows for an optimized waste-water treatment including the recirculation of wastewater in the melamine process, generation of clean process water after filtration and recovery of alkali, e.g. CaCO$_3$ in the causticizing process.

As described, the part of the thermally and/or otherwise treated mother liquor, which is not being recycled, can be directly discharged as waste water to a biological water treatment plant, into canal, drainage or river.

According to a further exemplary embodiment of the present invention at least parts of the waste water can however also be used for further purposes like cooling purposes, in particular as make up water in a cooling water supply.

In nearly any chemical plant cooling water for instance for condensers, product coolers or other coolers is needed. The melamine process requires for instance cooling water for cooling the mother liquor and/or the solid melamine. As cooling water usually river water, sea water or well water is used.

The cooling water is usually cooled down in cooling towers, where the warm cooling water is cooled down by contact with the ambient air in the process of evaporative cooling. The cooling is caused by evaporation of the water, what leads to a loss of water in form of evaporating water ($m_{ev}$).

Furthermore, due to the evaporation a concentration increase of components ($c_{cw}$) present in the cooling water occurs. This concentration increase can only be tolerated up to a certain extent since otherwise it can lead to blockages in the cooling unit. Therefore, water has to be discharged on a regular basis in way of the so called water blow down ($m_{bd}$).

These losses—evaporation and blow down—are compensated by the addition of make up water ($m_{mu}$). The make up water is the sum of evaporated water ($m_{ev}$) and water blow down ($m_{bd}$).

The concentration increase of the cooling water ($c_{cw}$) is therefore adjustable by the addition of make up water and depends on the quality of the make up water ($c_{mu}$) and the originally feed cooling water in the cooling water loop. Usually the concentration increase varies between 1.1, e.g. sea water and 10 e.g. spring water or demineralised water ($c_{cw}=1.1<c_m<10$).

The use of waste water as make up water enables the reduction of fresh water which needs otherwise to be fed into the cooling process. This is especially an advantage in geographical arid areas or in order to reduce the amount of polluted industrial water.

According to this embodiment of the invention at least parts or all of the waste water, preferably 20 to 100%, especially preferred 40 to 100% of the total amount of waste water, are used as make up water.

Beside the waste water also a second source of make up water like fresh water can be used. The ratio of waste water and fresh water used as make up water is preferably between 1:1 and 1:20, preferably between 1:2 and 1:8, most preferably 1:6.

The make up water is preferably mixed with at least parts of the cooled water. The ratio of make up water and cooled water is preferably between 1:8 and 1:100, preferably between 1:10 and 1:80, most preferably 1:30.

The mixture is then used for cooling purposes in a chemical plant, for instance in the melamine process.

The heated cooling water leaving the melamine process is then cooled in a cooling tower, whereby app. 3 to 10 t water, in particular 4 to 6 t water per ton of produced melamine are evaporated for providing the required cooling effect. The cooled water leaving the cooling tower is either partly mixed with the make up water and thus returned into the cooling cycle or partly discharged as water blow down.

In a further preferred embodiment the waste water used as make up water for a cooling process can also be waste water, which was not thermally treated beforehand.

Furthermore, the use of waste water as make up water is not reduced to a combination with the above described recycling methods, but can rather be applied independently to any process requiring cooling water.

BRIEF DESCRIPTION OF THE DRAWINGS

The invention will be illustrated in drawings with reference to working examples. They show.

DETAILED DESCRIPTION OF THE PREFERRED EMBODIMENTS

Example 1

Recycling of Alkaline Mother Liquor Without Further Treatment

The scheme of FIG. 1a shows the recycling path of alkaline mother liquor according to one embodiment of the invention.

Educts, in particular urea, are fed to the high pressure melamine process (1). 11 t/h of the melamine melt leaving the high pressure part are transferred to the wet part (2) of the melamine process comprising a quenching stage, where the melt is quenched with NaOH solution, and a crystallisation stage. 10 t/h of solid melamine with high purity are obtained as a consequence. The alkaline mother liquor likewise obtained in the crystallisation stage undergoes a thermal treatment in order to remove triazines present in the mother liquor. The thermal treatment process (3) comprises a thermal hydrolysis stage followed by a stripping stage for removing $NH_3$. 3 t/h of the stripped alkaline mother liquor are recycled to the wet part (2) of the melamine process; the remaining part of the stripped alkaline mother liquor is discharged.

In one specific embodiment according to FIG. 1a high pressure melamine plant which provides a total of 28 t/h thermally treated waste water allowed for a recycling of approximately 3 t/h waste water. Hence, the amount of discharged waste water was reduced from 28 t/h to 25 t/h.

Figure 1B:
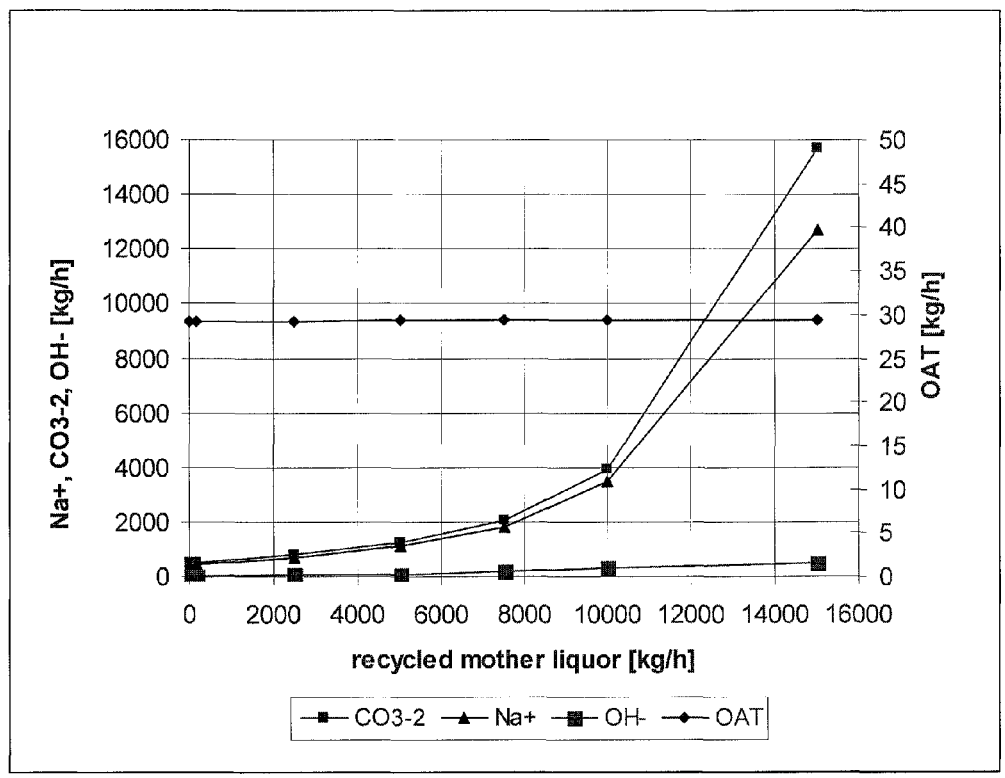
FIG. 1a Schematic view showing the cycle of alkaline mother liquor in a first embodiment of the present method FIG. 1b Diagram showing the effect of recycled alkaline mother liquor without adjusting the NaOH input FIG. 1c Diagram showing the effect of recycled alkaline mother liquor on the reduction of NaOH FIG. 1d Diagram showing the cost saving effect of the recycling method FIG. 1e Diagram showing the rise of pH-value without and with reduced NaOH amount added to the wet process FIG. 2 Schematic view showing the cycle of alkaline mother liquor in a second embodiment of the present method FIG. 3 Schematic view showing the cycle of alkaline mother liquor in a third embodiment of the present method FIG. 4 Schematic view showing the cycle of alkaline mother liquor in a fourth embodiment of the present method FIG. 5 Schematic view showing the cycle of waste water in a fifth embodiment of the present method

Diagram of FIG. 1b shows the effect of the recycled wastewater, i.e. recycled alkaline mother liquor, if the flow of caustic soda i.e. NaOH added to the mother liquor stream would not be adjusted. The concentrations of $Na^+$ and $CO_3^{2-}$ ions increase with the amount of treated waste water recycled to the wet part of the Melamine process, which would cause a rising pH (FIG. 1e) and could cause problems in the product quality. In contrast, the concentration of OATs stays at a constant level because of a good hydrolyser performance in the waste water treatment section.

Figure 1C:
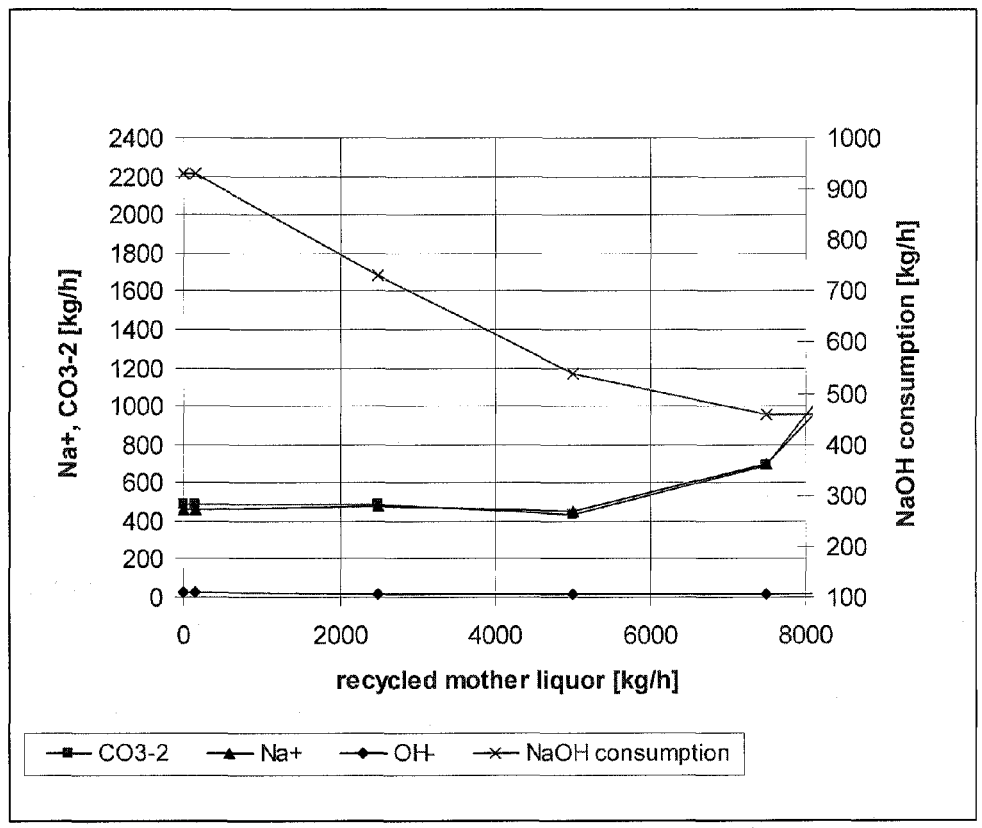
Figure 1D:
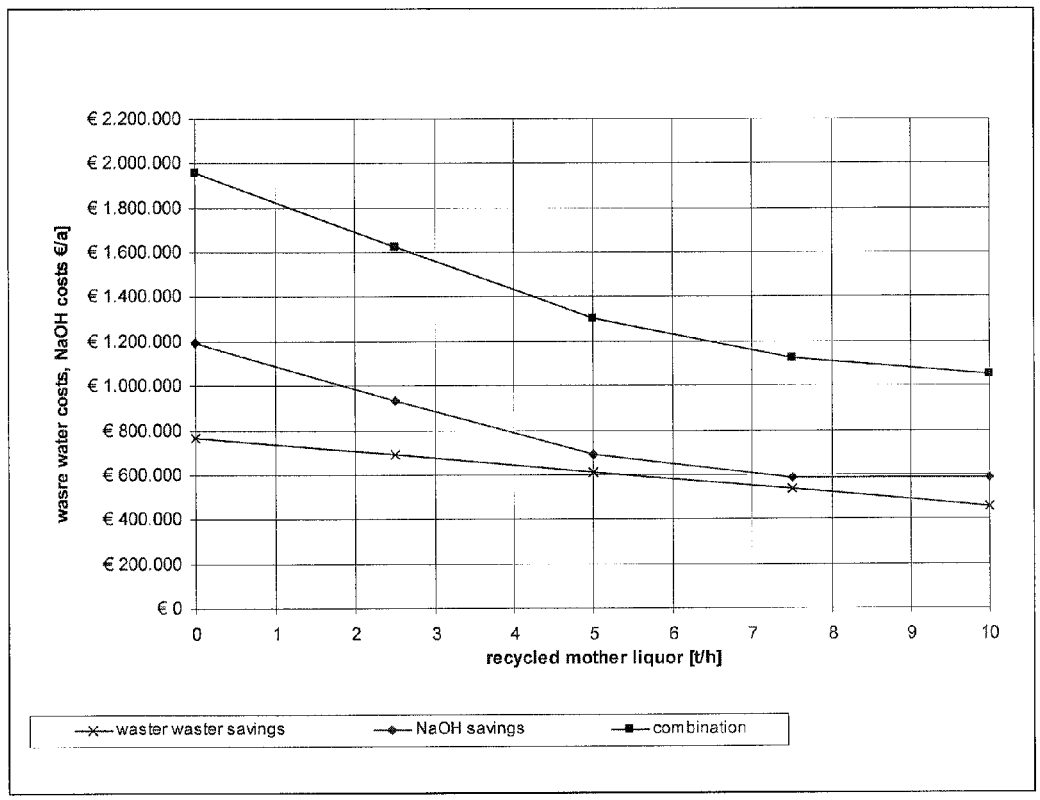

With the recycling of the alkaline mother liquor a reduction of fresh NaOH is feasible. Diagram of FIG. 1c shows the correlation between reductions of NaOH, and therefore NaOH costs, and the amount of recycled alkaline mother liquor. Also the amounts of $Na^+$ and $CO_3^{2-}$ ions are visualised which can be held on a constant level as a consequence of the reduction of NaOH (valid for a recirculation up to 6000 kg/h). It is evident that the effect for NaOH reduction is very significant up to a waste-water-recirculation of 6000 kg/h for cost saving. If recycling is done to a higher amount as 6000 kg/h the carbonate concentration in the wet process increases to much with possibly undesirable effects on melamine quality. In FIG. 1d the cost reduction of such a recycle stream can be seen (costs for NaOH ca. 300 €/t and waste-water 3.50 €/t).

Figure 1E:
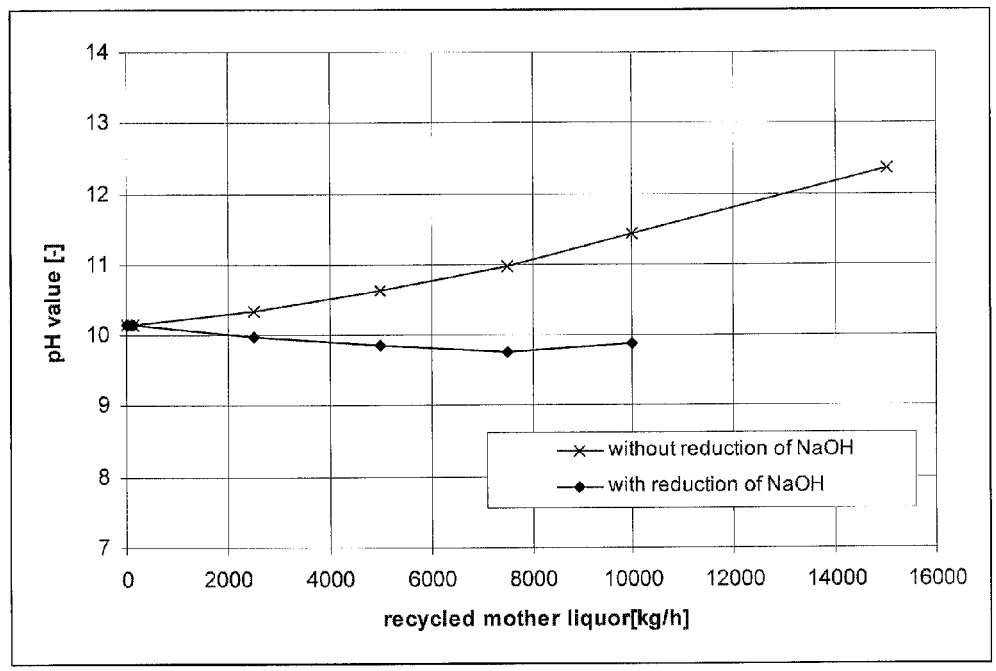

Besides the savings in fresh NaOH by recycling the alkaline mother liquor a considerable reduction of fresh water can also be achieved by the process of the invention. The reduction of for instance 2000 kg/h fresh water causes in turn a reduction of 2000 kg/h waste-water and 140 kg/h NaOH (FIG. 1e). The investment costs for implementation of the invention process are comparably low, as a pipe with simple control equipment is sufficient.

Example 2

Recycling of Alkaline Mother Liquor Comprising a Filtration Step

Figure 2:
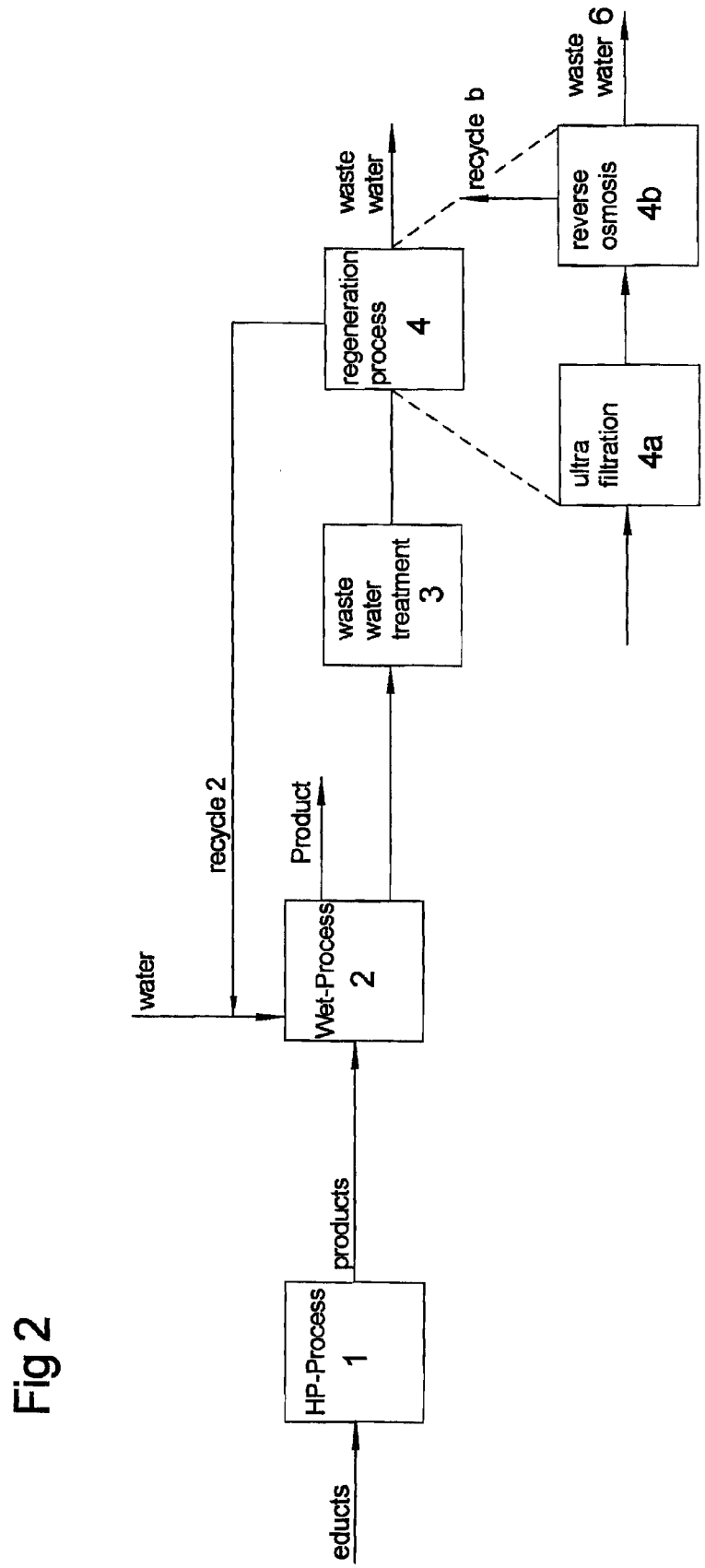

FIG. 2 shows the scheme of a second embodiment with the regeneration step (4) comprising an ultrafiltration step (4a) and reverse osmosis step (4b).

The thermally treated melamine waste water (3) is recovered with the help of a reverse osmosis unit (4b) in combination with an ultrafiltration stage (4a). The ultrafiltration step (4a) removes particles that cause fouling from the waste water feed prior to reverse osmosis (4b). Subsequently, reverse osmosis (4b) splits the waste water into the permeate, that is nearly free from dissolved species, in particular, $Na_2CO_3$ and $NaHCO_3$, and the retentate that contains most of the dissolved species with significantly higher concentrations than in the waste water feed.

The permeate, which essentially consists of pure water, is recycled to the wet process of the melamine plant. Permeate recovery in the form of pure water by reverse osmosis reaches up to 80% depending on pH and feed concentration. This means that the amount of discharged waste water is reduced to approximately 6 t/h from a total of 28 t/h, whereas the remaining 22 t/h of permeate are recycled to the wet section.

Example 3

Recycling of Alkaline Mother Liquor Comprising a Causticizing Step

Figure 3:
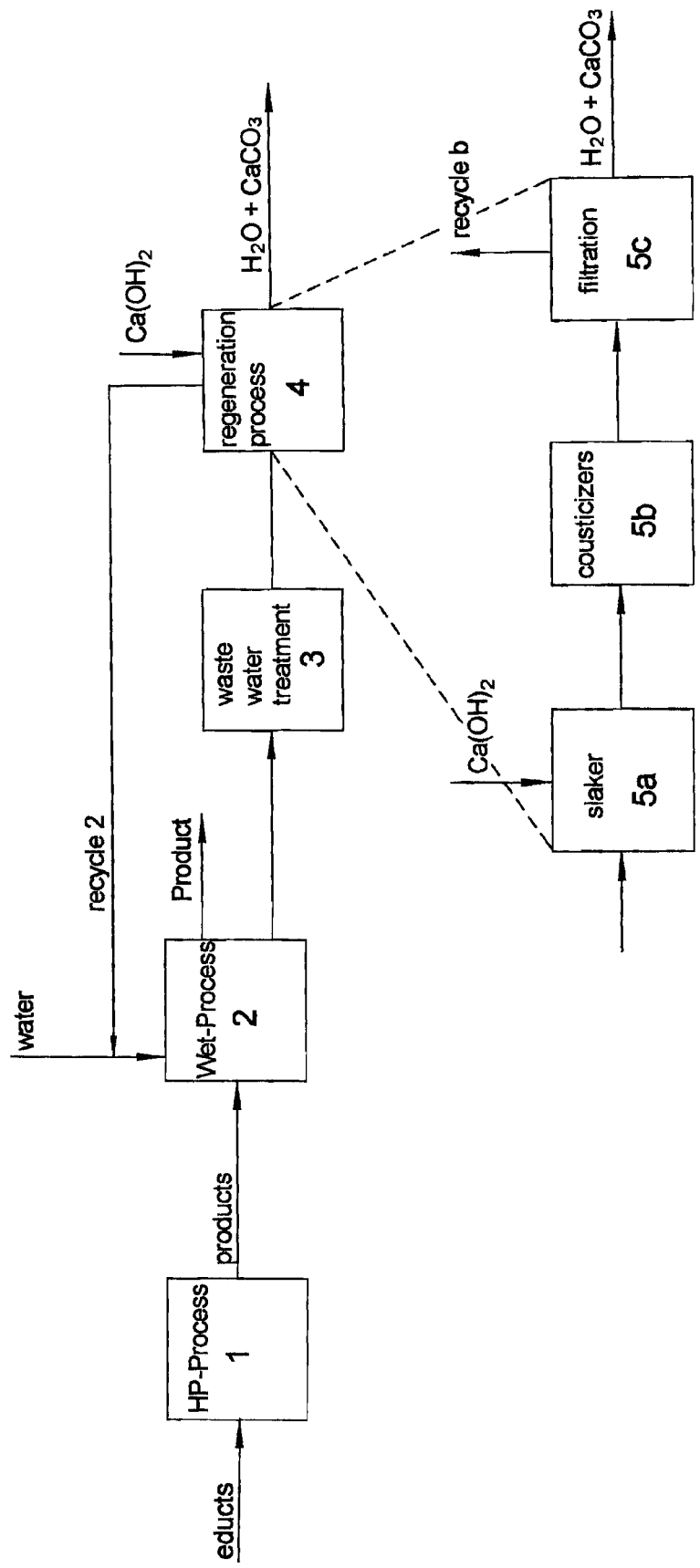

FIG. 3 shows the scheme of a third embodiment with a regeneration process (5) comprising the steps of adding $Ca(OH)_2$ (5a), caustification (5b) and filtration (5c).

As the waste water after thermal treatment 3 contains approximately 3% of the component $Na_2CO_3$, the challenge for the treatment is to recover NaOH with $Ca(OH)_2$. Dependent on the residence time the causticizing reaction 5b has a conversion rate between 90 and 100 percent. The advantage of this treatment is the regeneration of NaOH and related to that the reduction of waste-water with a high efficiency. A reduction of waste-water up to 80% is achieved. The remaining non-recycled waste-water contains a high amount of solid $CaCO_3$, which can be separated and used in other processes (NPK or CAN fertilizer processes).

In an embodiment 20 g/L CaO (0.4 mol/L) are added to 100 mL of melamine waste water containing 30 g/L $Na_2CO_3$ (0.3 mol/L—giving a pH-value of 10.4). The molar concentration reaction is stoichiometrically chosen to enable a maximum conversion of $Na_2CO_3$ to NaOH (see reaction equations above). The reaction time is two hours at a temperature of 20° C. and a pressure of 1 atm.

An increase of the pH-value to between 12.5 and 13.5 could be detected after the reaction due to the formation of free NaOH. The analysis is carried out using an Ion chromatography whereby no $Ca^{2+}$-ions are found in the dissolution. The solid matter ($CaCO_3$ and $Ca(OH)_2$) are easily filtrated. For a complete separation of the solid phase a centrifuge is used. The clear solution containing NaOH is almost completely recycled to the wet part of the melamine process.

Example 4

Figure 4:
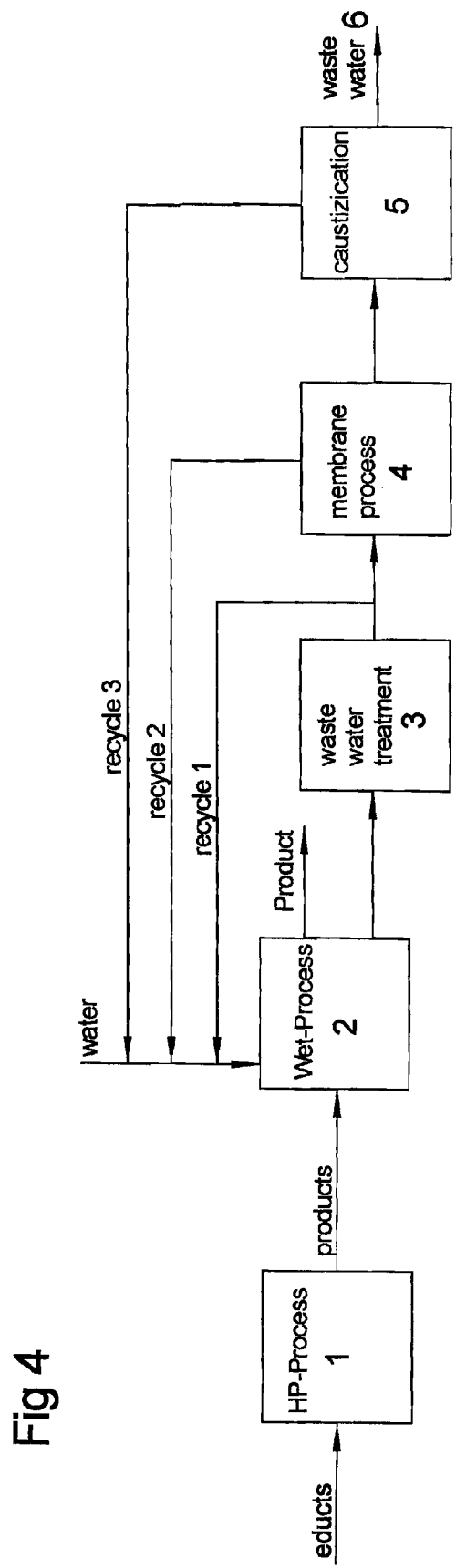

Recycling of Alkaline Mother Liqor Comprising a Filtration Step and a Caustification Step The scheme of FIG. 4 shows a fourth embodiment of the invention whereby the above described embodiments are combined. Such a combination of all three above described embodiments is the most efficient approach.

According to the first embodiment (FIG. 1) 3 t/h of a total of 28 t/h thermally treated melamine waste water (3) is recycled to the wet process (2) reducing the waste water to 25 t/h (stream recycle 1) as described in Example 1 (FIG. 1a).

The remaining, non-recycled waste water is treated in a reversed osmosis (4b) with an upstream ultrafiltration stage (4a). As described in Example 2 the reduction of waste water in this embodiment reaches up to 80%. Hence in this case, 5 t/h (20%) of a concentrated solution of $NaHCO_3$ and $Na_2CO_3$ remain in the retentate whereas 20 t/h (80%) of the permeate, which essentially consists of pure water, is recycled to the wet process (stream recycle 2).

Subsequently the retentate is submitted to the third regeneration step 5, namely the causticizing reaction (5a,b) at a pressure of 1 atm and a temperature of 20° C. (described in Example 3), whereby CaO is added. The final solid is a mixture of $Ca(OH)_2$, $CaCO_3$, $Na_2CO_3$, traces of melamine and side products, which is removed by centrifugation or filtration (5c) from the liquid phase. The liquid phase stream recycle 3 contains a concentrated NaOH-solution which is recycled to the wet part of the melamine process.

With this embodiment of the invention the NaOH consumption is be reduced up to 70%.

Example 5

Use of Waste Water as Make Up Water

Figure 5:
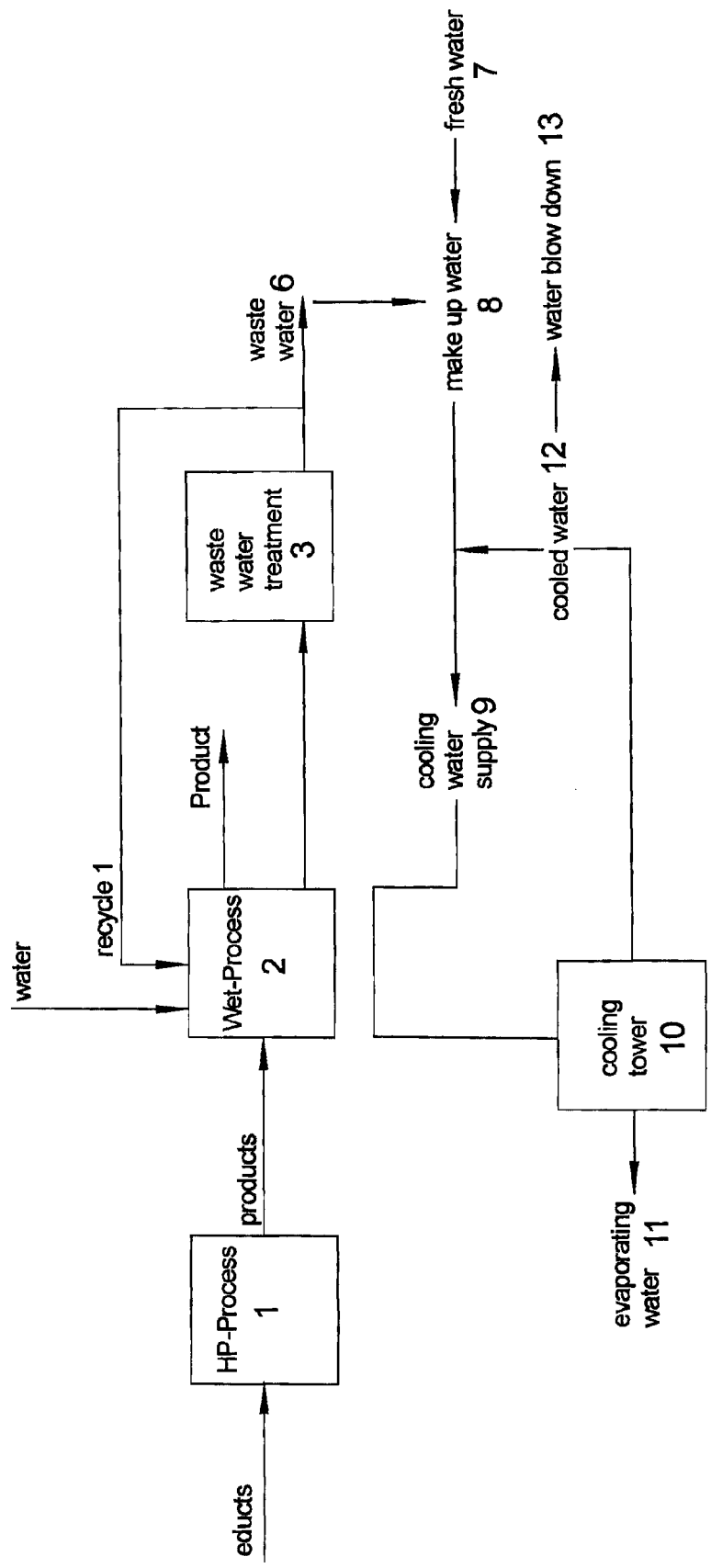

FIG. 5 shows the a fifth embodiment of the invention in which the waste water (6) accumulating in a process according to FIG. 1a is at least partly used as make up water (8). The waste water can of course also stem from a process according to FIG. 2, 3 or 4 or from any other process providing waste water.

Additionally, fresh water (7) is added as a second source of make up water. Together with the water blow down (12) the make up water is supplied as cooling water (9) to the melamine plant, for instance to the wet part (2) of the melamine synthesis process. In order to cool the heated cooling water (9) the same is transferred to a cooling tower (10), where the cooling water is cooled down due to water evaporation (11). The cooled water (12) accumulating in the cooling tower is subsequently discharged, whereby parts of the cooled water (12) are mixed with make up water (8) and thus, kept in the cooling cycle. Another part of the cooled water is discharged as blow down water (13).

A melamine plant of commercial size requires approx. 450 m³ of cooling water per ton of produced melamine. In the cooling tower of that said plant size approx. 7 t of water per ton of produced melamine are evaporated to provide the required cooling for the melamine process. In case the concentration in the cooling water $c_{cw}$ is 3 times higher than the concentration of the make up water $c_{mu}$ the required amount of blow down water is 3.6 tons per ton of produced melamine. Considering equation the $$m_{mu}=m_{ev}+m_{bd} \quad (1)$$

the amount of make up water required is therefore 10.6 tons per ton of produced melamine.

A melamine plant of commercial size discharges approx. 2.6 tons of waste water per ton of produced melamine.

The make up water used in this process therefore consists of 2.6 tons of waste water per ton of produced melamine melt and 8 t of fresh water. By using the 2.6 tons of waste water as a part of the make up water, the amount of fresh make up water can therefore reduced to 8 tons per ton of produced melamine.

The invention claimed is:

1. A method for recycling water in a melamine production process comprising:
   a wet process comprising an aqueous treatment of a melamine melt from a melamine synthesis plant with an aqueous alkali containing solution, wherein the aqueous treatment comprises quenching of a melamine melt from a melamine synthesis plant after off-gas separation with NaOH or KOH solution, and crystallisation for providing solid melamine and a triazine containing alkaline mother liquor,
   a wastewater treatment process comprising thermal treatment of said triazine containing alkaline mother liquor, wherein the thermal treatment comprises a thermal hydrolysis stage performed at a temperature of between 200 to 260° C., and
   a recycling process, wherein at least parts of the thermally treated alkaline mother liquor are being recycled to the wet process.

2. The method according to claim 1, wherein the part of the thermally treated alkaline mother liquor which is not being recycled to the wet process is discharged as wastewater.

3. The method according to claim 1, wherein the thermally treated alkaline mother liquor is subjected to filtration before at least parts of it are being recycled to the wet process.

4. The method according to claim 3, wherein the thermally treated alkaline mother liquor is fed to at least one membrane filtration unit (MF), is separated in the membrane filtration unit (MF) into a permeate and retentate, whereby at least parts of the permeate are recycled to the wet process.

5. The method according to claim 3, wherein the membrane filtration unit comprises an ultrafiltration and reverse osmosis.

6. The method according to claim 1, wherein up to 80 wt % of the thermally treated alkaline mother liquor and/or the permeate are recycled to the wet process.

7. The method according to claim 1, wherein the thermally treated alkaline mother liquor is subjected to causticisation before at least parts of it are being recycled to the wet process.

8. The method according to claim 7, wherein $Ca(OH)_2$ or lime is added to the thermally treated alkaline mother liquor.

9. The method according to claim 7, wherein the causticised solution is subjected to a solid separation step, and recycling at least parts of the NaOH enriched supernatant to the wet process.

10. The method according to claim 2, wherein the wastewater is fed to and separated in a membrane filtration unit (MF) into permeate and retentate, whereby at least parts of the permeate are recycled to the wet process.

11. The method according to claim 10, wherein the permeate leaving the membrane filtration unit is causiticised, the causticised solution is then subjected to a solid separation step, and at least parts of the supernatant are recycled to the wet process.

12. The method according to claim 2, wherein at least parts of the wastewater are used for cooling purposes.

13. The method according to claim 12, wherein said parts of wastewater are used as make up water.

14. The method according to claim 7, wherein slaked lime is added to the thermally treated alkaline mother liquor.

15. The method according to claim 7, wherein the causticised solution is subjected to filtration and recycling at least parts of the NaOH enriched supernatant to the wet process.

16. The method according to claim 10, wherein the permeate leaving the membrane filtration unit is causiticised, the causticised solution is then subjected to precipitation or filtration, and at least parts of the supernatant are recycled to the wet process.

* * * * *